(12) United States Patent
Hugo

(10) Patent No.: US 6,290,502 B1
(45) Date of Patent: Sep. 18, 2001

(54) METHOD, DEVICE AND MEDIUM FOR THE REMOVAL OF CARIES IN A CAVITY

(75) Inventor: Burkhard Hugo, Hettstadt (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 0 days.

(21) Appl. No.: 09/485,075
(22) PCT Filed: Jun. 4, 1999
(86) PCT No.: PCT/EP99/03884
§ 371 Date: Feb. 3, 2000
§ 102(e) Date: Feb. 3, 2000
(87) PCT Pub. No.: WO99/63904
PCT Pub. Date: Dec. 16, 1999

(30) Foreign Application Priority Data

Jun. 5, 1998 (DE) .............................. 198 25 262

(51) Int. Cl.⁷ ........................................ A61C 5/00
(52) U.S. Cl. .................. 433/215; 433/216; 433/226; 433/88
(58) Field of Search .................... 433/215, 216, 433/226, 80, 88

(56) References Cited

U.S. PATENT DOCUMENTS

| | | | |
|---|---|---|---|
| 3,919,775 | 11/1975 | Malmin | 32/57 |
| 3,943,628 * | 3/1976 | Kronman et al. | 433/216 X |
| 5,018,970 * | 5/1991 | Stordahl | 433/116 X |
| 5,531,722 * | 7/1996 | Van Hale | 433/116 X |
| 5,547,376 * | 8/1996 | Harrel | 433/116 |
| 5,601,430 | 2/1997 | Kutsch et al. | 433/215 |
| 5,697,787 * | 12/1997 | Schumacher | 433/226 |
| 5,865,620 * | 2/1999 | Kutsch | 433/88 |
| 5,951,285 * | 9/1999 | Ho | 433/88 X |

FOREIGN PATENT DOCUMENTS

| | | |
|---|---|---|
| 880 630 | 5/1952 | (DE) . |
| 42 09 191 A1 | 5/1993 | (DE) . |
| 1 469 400 | 4/1977 | (GB) . |

OTHER PUBLICATIONS

International Search Report for PCT/EP99/03884 dated Dec. 12, 1999.

* cited by examiner

Primary Examiner—Nicholas D. Lucchesi
(74) Attorney, Agent, or Firm—Marshall, O'Toole, Gerstein, Murray & Borun

(57) ABSTRACT

The invention relates to a method for the removal of caries (4) in a cavity (7), in which a flowable medium (11), which contains a caries (4)-dissolving substance and/or solid particles (13), is introduced into the cavity (7) and for improving the effectiveness the medium is acted upon with oscillations by means of an oscillation part (14) which is applied in the medium (11) located in the cavity (7).

24 Claims, 2 Drawing Sheets

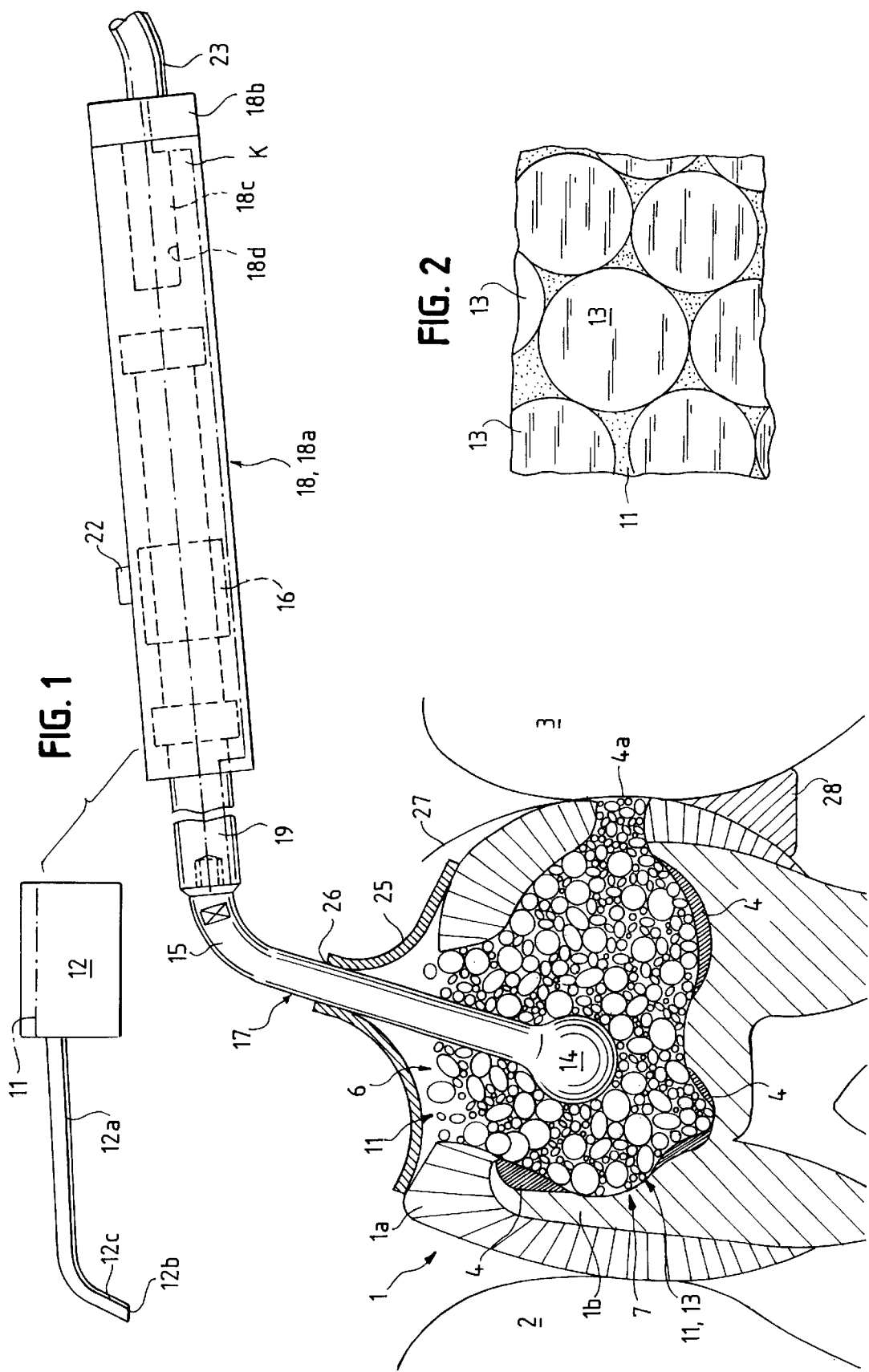

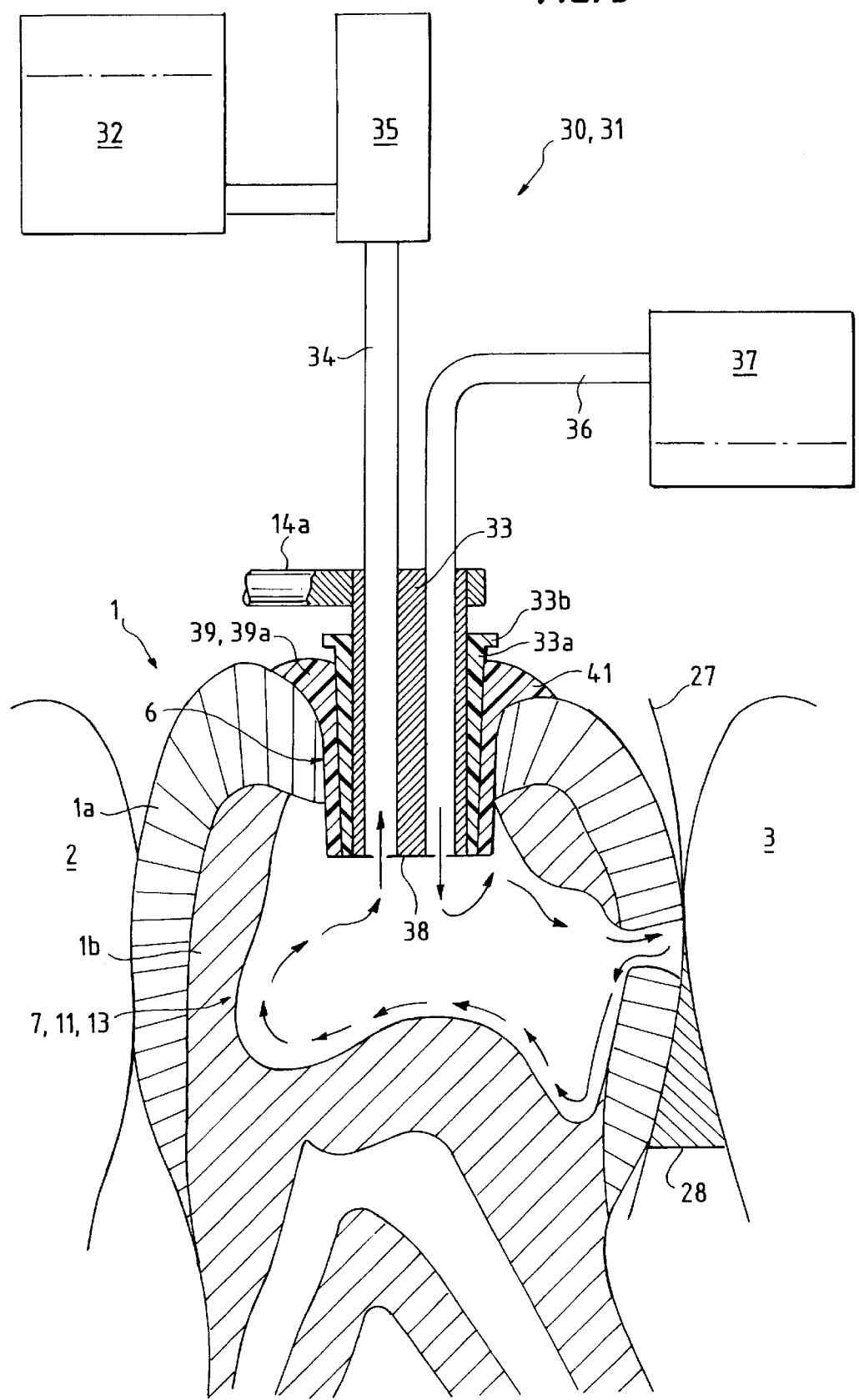

METHOD, DEVICE AND MEDIUM FOR THE REMOVAL OF CARIES IN A CAVITY

The invention relates to a method, a device and a medium for the removal of caries in a cavity.

A conventional measure for removing caries consists in that they are removed by machining, e.g. with rotating or oscillating tools, which are held by means of a shaft in a handpiece and in functional operation are moved against the site to be worked. When the caries are deeply lying, this measure is problematic for many reasons. On the one hand it requires a large access opening in order to make it possible for the dentist to have a view into the cavity, so that he is able to determine where caries are located and whether the caries have been completely removed. This is difficult to check visually, and therefore there remains the danger that the caries are insufficiently removed or that healthy tooth substance is removed. Further, the caries may have bizarre spatial forms, so that it is necessary also the remove neighbouring healthy zones or tooth substance with the tool, in order to be able to completely remove the caries.

The above-described disadvantages are then even more grave when a deeply lying caries is enlarged in the tooth and has only a small access opening which is surrounded by healthy tooth tissues. With the known measures for the removal of caries, in addition to the above-mentioned disadvantages, it is necessary to create a sufficiently large access opening, whereby further healthy tooth substance is destroyed.

Although proposals have already been made to remove caries by means of a liquid or gel-like medium, which contains a substance which dissolves caries, these media are insufficient in their effect. Thereby it is to taken into account that the removal of caries should take place in one treatment session, in order to be economic.

The object of the invention is to find a method and a device of the kinds concerned which make it possible to purposively work surface regions.

With the method in accordance with the invention, a medium is employed which contains a substance which dissolves caries and/or contains solid particles, which is introduced into the cavity and which is acted upon with oscillations by means of an oscillation part placed into the medium located in the cavity. Hereby, the effectiveness of the medium is improved in many respects. On the one hand, the penetration of the medium into the cavity and also into small crevices is improved, so that it is also brought to poorly accessible locations of a cavity and can be effective. On the other hand, by means of the oscillations, the effectiveness of the medium is improved and intensified. This applies both for the alternative in which the medium contains a caries-dissolving substance and also for the alternative in which the medium contains solid particles. In the first case, the improved effectiveness is the result of the effectiveness of the caries-dissolving substance being improved by means of the oscillation. In the second case, the solid particles are accelerated by means of the oscillations, whereby the transfer of oscillations extends up to the periphery of the medium, due to the mass of the medium, and the particles located there impact against the wall of the tooth bounding the cavity and remove in particular the tissue infected with caries, which is softer than healthy tissue. The removal effect at healthy tissue, which is harder, is only very slight. This is advantageous because the healthy tissue should be conserved.

The above-described method is suitable both in a closed system, in which the cavity is covered over, and also in an open system, in which the cavity is not covered. The latter is particularly advantageous because a very simple method is involved in which there is no need to provide for a cover, which is naturally linked with a corresponding outlay of effort. In any event, the open system is intended for such treatment situations in which the cavity is open at the upper side. It is naturally also possible to use this method in a closed system, in which the opening of the cavity or access cavity is closed.

Another embodiment of the method according to the invention is intended for a closed system. With this method, the desired improvement of the effectiveness of the medium is achieved in that the medium is supplied to the cavity continuously, at least for periods, e.g. in flowing movement. This leads to a more intensified exchange of the medium at the wall of the cavity and to an improvement of the performance of the medium because effective substance is continuously brought to the wall and to the caries. Further, by means of the flow, the contact between the medium and the cavity wall is improved. This applies in particular for the alternative in which the medium contains hard particles instead of a caries-dissolving substance, which particles are capable of removing the relatively soft tissue, infected with caries, due to the flow. As with the above-described method, the healthy tissue is also conserved with this method.

With both methods in accordance with the invention a particular advantage is to be seen in that the improved effectiveness is attained independently of the shape and size of the cavity, whereby in substance only the tissue infected with caries is removed, whilst the healthy tissue is retained. This is achieved in that the flowable, liquid or pasty medium is shape independent and can therefore also penetrate into bizarre and constricted cavity shapes and carry out effective material removal, without neighbouring regions of healthy tooth substance simultaneously being removed, as is the case with the state of the art.

Some features of the invention improve the effectiveness of the medium. In the first case in that the particles are abrasive at their outer surfaces and in the second case in that the particles, due to their mutual contacting, directly transfer to one another the oscillations and the mass forces brought about thereby, so that the particles located at the periphery are effective.

The above-described advantages apply also for the devices in accordance with the invention, which are distinguished by a simple and functional construction, which make possible in a simple manner a covering or sealing of the cavity and make possible an economic removal of the caries and also an advantageous accessability and manipulability also at inaccessible sites in the mouth.

The above-described advantages apply also for the medium in accordance with the invention, which is suitable for mechanically removing body tissue, in particular caries. For this purpose, the medium in the cavity is to be set in movement so that the solid particles contained therein achieve frictional contact or impact contact with the wall of the cavity and thereby remove the body tissue, in particular caries. The movement may be realized in that the medium is set into oscillation or into flow.

The medium can be improved in that a caries-dissolving substance is mixed in. By these means, the medium is not only mechanically but also chemically effective, whereby the chemical effectiveness is independent of the flow and is also effective with non-flowing medium. By means of the flow, however, also the chemical effectiveness is promoted.

A further improvement of the medium is then attained when the particles are abrasive. This can be achieved through particles which are of an abrasive material or which have at their surface an abrasive material, e.g. are occupied or coated with abrasive grains.

Below, the invention and further advantages which can be achieved thereby will be described in more detail with reference to a plurality of preferred exemplary embodiments and to simplified drawings, which show:

FIG. 1 a tooth in vertical section during treatment with the first method in accordance with the invention, with an open system;

FIG. 2 a detail of FIG. 1, in an enlarged illustration;

FIG. 3 a tooth in vertical section during the removal of caries in accordance with the second method in accordance with the invention, with a closed system.

The tooth, generally designated 1, is located between two neighbouring teeth 2, 3, whereby the tooth 1 has a deep-lying caries 4, which by means of a tapered connection zone 4a can emerge at a side or upwardly at the chewing surface of the tooth 1. In the illustrated example, the connection zone 4a is arranged approximately and thus is inaccessible from the side.

In the illustration in FIG. 1, the method is in a stage in which the carious site is broken into occlusally or is conventionally pre-prepared, e.g. with a rotating tool, so that an access opening 6, in this case an occlusal opening, is present. In the region of the deep-lying caries 4, located both in the enamel la and also in the dentin 1b, a cavity 7 is present which may be a natural cavity 7, that is created by the caries 4, or a cavity 7 created by means of a pre-preparation. As FIG. 1 clearly shows, the cross-sectional dimension of the access opening 6 is substantially smaller than the cross-sectional dimension of the cavity 7 located therebelow. In the region of various wall locations of the cavity 7, caries 4 are still present, the layer thickness of which is illustrated relatively thinly, but which may also be substantially thicker, in particular when the method in accordance with the invention is employed in the region of a natural cavity, without pre-preparation.

For carrying out the method in accordance with the invention, there is present a medium 11 of liquid or pasty consistency, e.g. gel consistency, which contains a caries-dissolving substance and is available in a supply container 12, shown to a reduced scale, out of which the medium 11 can be introduced into the cavity 7, e.g. by means of a cannula 12a which at its free end has an exit opening 12b for the medium 11, in particular at the end of an angled cannula limb 12c, out of which the medium 11 can be transported, e.g. by means of manual pressing together of the supply container 12 of elastic material, in particular plastics.

The caries-dissolving substance may be, e.g. sodium hypochloride in combination with amino acid, with a strongly basic pH value.

It is advantageous if the medium 11 further contains solid or hard particles 13, the size of which may be uniform or vary and be e.g. about 0.001 mm to about 0.1 mm, in particular about 0.1 mm. The particles 13, which may be e.g. a mixed-in powder, are preferably abrasive at their surfaces. Such abrasive materials are e.g. aluminum oxide, silicon carbide, quartz, glass, salts and the like. Abrasively coated particles are also suitable, e.g. of plastics or glass. The particles may have an irregular shape or spherical shape.

Further, for carrying out the invention, an oscillating body 14 is provided, the cross-sectional size of which is smaller than the access opening 6 and which is located at the end of a shaft 15, preferably shaped or arranged to be angled, and which can be set into oscillation by means of an oscillation generator 16, preferably in the sonic or ultra-sonic range. The oscillation body 14 may in its cross-sectional size be the same or greater than the cross-sectional size of the shaft. With the present configuration, the oscillation body 14 is thickened with reference to the shaft 15 and is preferably spherical with or without laminations. An elongate or rod-shaped handpiece 18 serves for holding the so formed tool 17, in which handpiece a handpiece shaft 19 is mounted so as to be capable of oscillation and can be set into oscillation by means of an oscillation generator 16 arranged in the handpiece 18. The oscillation generator 16 or vibration drive generates short stroke oscillations in the sense of a vibration with a frequency preferably lying the sonic or ultra-sonic range, whereby the oscillations or amplitudes may be elliptically or circularly orbital, whereby the amplitude direction preferably changes spatially, that is in all directions.

The drive power of the oscillation generator 16 is preferably variable and thus adaptable to different working conditions. For this purpose a setting member 22 is provided which is preferably arranged on the handpiece 18 in particular at its outer surface, and is mounted there e.g. slidably. For energy supply there serves a flexible supply line 23 which extends from the rearward end of the handpiece 18 to a supply and control apparatus which is not illustrated.

The handpiece 18 consists of a grip piece 18a and a rearward connection part 18b which are releasably connected with one another by means of a quick coupling, here a plugin-turn coupling. The coupling K has a cylindrical insertion pin 18c, here at the connection part 18b, onto which the other part can be inserted with an insertion recess 18d and which can be secured by means of a non-illustrated latching device which can be unsnapped.

The tool shaft 15 is preferably releasably connected with the handpiece shaft 19. A screw connection may serve for this purpose.

For switching on the oscillation generator 16 there is provided a switch (not shown), e.g. at the handpiece 18 or remote therefrom as a foot-switch.

With the present exemplary embodiment, the vibration or oscillation drive has a frequency of about 4 kHz to 8 kHz, about preferably 6 kHz, whereby in the region of the tool 17 or oscillation body 14 an amplitude of the preferably three-dimensional oscillations is provided of about 0.05 mm to 0.2 mm, in particular 0.1 mm. Thereby, the thus constituted control device may be so configured that a setting of the oscillation power in the above-mentioned range or also a setting above the range is possible, so that if appropriate considerably greater amplitudes can be set, e.g. amplitudes up to about 0.5 mm.

For the removal of the caries 4, the medium 11 is introduced or washed in to fill the cavity. Then, the activation of the medium 11 is effected by means of the oscillation body 14, which due to the above-described tool shape can, using the handpiece 18, be readily introduced through the mouth opening into the medium 11 located in the cavity 7 and switched on. By means of the transfer of oscillations, the medium 11 is set into oscillation and its effect is promoted, and its capacity for dissolving caries is increased. In this case, primarily the chemical effectiveness of the caries-dissolving substance is involved.

When the medium 11 contains particles 13, it is furthermore physically effective. This is based on the fact that the oscillation energy is transformed into kinetic energy for acceleration of the particles 13 and these impact against the carious substance and thereby remove that substance. The particles are in particular effectively accelerated and made turbulent when the number of particles 13 in the medium 11 is so great that the particles lie against one another and the transfer of oscillations is effected directly. This is illustrated in FIG. 2, which shows the particles 13—formed to be equal or unequal in their cross-sectional size—in positions abutting against one another. Between the particles 13, however, the medium 11 can also be located. The active caries removal can also be effective by means of an abrasive coating of the particles 13.

Since the tissue infected by the caries 4 is softer than healthy tissue, with a method in accordance with the invention the carious tissue is in particular removed and taken away. In contrast, the healthy tissue is conserved.

By means of the method in accordance with the invention not only is the carious tissue removed but there is also achieved an advantageous bonding preparation of the obturation surfaces and/or obturation of the cavity 7.

Depending upon the quantity of carious tissue, the method in accordance with the invention can be repeated. Between the individual method stages, or after the method in accordance with the invention, the cavity 7 is emptied and cleaned, e.g. though suction, through rinsing, blowing and the like.

With the method in the open system, the access opening 6 can be closed by means of a cover 25 attached to the tool shaft 16, which cover may be a flange-shaped closure part e.g. in the shape of an outwardly round disk having a central hole 26 with which it sits and is fixed on the tool shaft 15, e.g. by means of clamping tension. The cover 25 or the disk are preferably of elastic material such as plastics or rubber, so that the free edge of the disk is capable of adapting to the tooth surface. Preferably, the disk is conical or truncated conical in shape, whereby it is stabilized against folding over. With the aid of the flange-shaped cover 25, the cavity 7 can be closed and thus such a tool 17 is suitable also for the treatment of a cavity which is open to the side or below. Even in such positions, the medium 11 cannot self-actingly run out of the cavity 7 when it is covered over. In such cases it is advantageous to use a medium 11 of pasty consistency or a gel-form medium 11, which is however suitable also for a position in accordance with FIG. 1. The cover 25 may be freely displaceable in the longitudinal direction of the tool shaft 15 for the purpose of adaptation to the penetration depth of the tool or oscillation body 14 in the tooth. It is also advantageous to arrange the cover 25 on the tool shaft 15 displaceably and selectively fixably. This can be achieved by means of clamping tension with which the edge of the hole 26 presses against the tool shaft 15.

With the method in accordance with the invention, if appropriate, the tooth enamel caries 4 can also removed in the connection zone 4a, which in the present exemplary embodiment opens out approximally. Such openings are, before the introduction of the medium 11 into the cavity 7, covered over on the outside, e.g. by means of a bandage or a closure leaf 27 (metal matrix), which e.g. by means of a wedge 28 can be fixed in the region between the teeth.

With the exemplary embodiment according to FIG. 3, in which the same or similar parts are provided with the same reference signs, the removal of the caries 4 is effected on the one hand in the closed system and on the other hand with at least a period of continuous flow of the medium 11 and/or likewise by means of an activation of the medium 11 through oscillation.

The main parts of the device 30 are a feed device 31 for feeding the medium 11 from a supply container 32 to a rod-shaped connection part 33 through a supply line 34, in which a pump 35 is located. From the connection part 33, a discharge line 36 extends to a collection container 37. The supply line 34 and the discharge line 36 open at the free end face 38 of the connection part 33, whereby they penetrate the latter preferably axially. The connection part 33 may sit in a sleeve 33a or may form this sleeve 33a, which can be put in place directly in the access opening 6 or can be put in place in a second connection sleeve 39 which is of elastic material, in particular rubber or plastics, and can be placed and fixed in the access opening 6, preferably by means of radial clamping tension, and in particular has an outer flange 41 which bears outwardly on the tooth 1 and prevents a sliding into the tooth. The adaptation of the tooth opening to the connection piece 35 can be effected by means of standard pre-preparation. With individual access cavities, the sealing is effected by means of a provisional filing material (e.g. a "provisional" plastics, polymerized by light).

It is advantageous to form the connection part 33 or the first connection sleeve 33a conically towards its free end, and to form the second connection sleeve 39 correspondingly conically inwardly, in order to facilitate the connection and also here to bring about a clamping connection upon placement. The connection sleeve 33a or the connection part 33 may preferably likewise have a flange 33b for limiting the insertion depth. In particular when the first connection sleeve 33a or the connection part 33 is provided for a direct engagement in the access opening, it is advantageous to form them of an elastic material such as rubber or plastics, whereby the sealing and clamp seating is improved.

By means of the pump 35 or a downstream system, e.g. a Bernoulli jet, the liquid is in rapid alternation expelled under pressure and drawn in. These alternating load movements activate the solution or strengthen its effect by means of imploding cavitation bubbles.

For carrying out the method, the connection part 33 is connected in the above-described manner with the access opening 6 and the medium 11 fed into the cavity 7, whereby with this method a plurality of measures are available in order to improve the effectiveness of the medium and its performance.

When the medium 11 only has the caries-dissolving substance, the effectiveness and performance can be promoted in that the medium 11 is fed continuously or periodically, or at intervals, whereby during the feeding a continuous movement and flow take place which improve the effectiveness of the medium 11.

When the medium 11 contains only particles 13, the medium 11 is continuously fed whereby the particles 13 are mixed during the flowing, impact against the walls of the cavity 7 and remove the caries through impact effects.

When the medium 11 contains the caries-dissolving substance and the particles, the effectiveness can be correspondingly multiplied by means of feeding.

Additionally, the effectiveness can be promoted in that the connection part 33 and/or the first connection sleeve 33a or the supply line 34 and/or the discharge line 36 are, with an oscillation part 14a, acted upon by means of oscillations, whereby these oscillations are transferred to the particles and increase the effectiveness by means of the vibration effect of the particles 13.

Furthermore, the effectiveness of the medium 11 can be increased in that the pressure in the medium 11 is varied. This can be effected in a simple and advantageous manner by means of the pump 35, e.g. in that this is formed by means of a piston of a pressure pump, which upon the advancing stroke of the piston increases the pressure and on the return stroke decreases the pressure or even generates a partial vacuum. Similar pressure differences can be attained by means of a rotating piston functioning in accordance with the Wankel rotating piston principle, as feeding means for the pump 35.

It is thus shown that the effectiveness of the medium 11 can be altered by means of variation of its composition and can be promoted through the application of the above-described additional measures.

During the feeding of the medium 11 by means of the feed device 31, the medium 11 is mixed and made turbulent in the cavity 7, whereby the caries-dissolving substance in contact with the walls of the cavity 7, and/or the particles located there, dissolve or remove the caries 4. An example of the flow which thereby takes place is indicated in FIG. 3 by means of arrows. The medium 11 fed into the cavity 7 thereby flows through the discharge line 36 into the collection container 37. The opening of the line 36 may be secured by means of sieve against the flowing away of the particles 13 out of the cavity 7.

With all above-described exemplary embodiments, after the dissolving and/or material removal of the caries 4, the cavity 7 is cleansed, which may be effected by means of rinsing and/or blowing. Thereafter, the cavity 7 can be individually closed by means of a suitable filling material. The free outer surface form of the filling material in the region of the access opening 6 can be adapted to the form of a previously prepared imprint.

What is claimed is:

1. Method for removing caries in a cavity, comprising the steps of:
   (a) introducing a flowable medium containing at least one of a caries-dissolving substance and solid particles into the cavity;
   (b) introducing an oscillation element into the medium in the cavity; and
   (c) acting upon the medium with oscillations by said oscillation element.

2. Method of claim 1 wherein the medium contains abrasive solid particles.

3. Method of claim 1 wherein the medium contains solid particles in sufficient quantity that the particles mutually contact one another in the cavity.

4. Method of claim 1 wherein when the cavity is initially of insufficient size to carry out said method, and the method comprises the further step of pre-preparing the cavity.

5. The method of claim 4 wherein said pre-preparing step is carried out with a rotating or oscillating tool.

6. Method according to claim 1, wherein the medium contains a caries-dissolving substance and/or solid particles.

7. Method according to claim 6 wherein the particles are abrasive.

8. Method according to claim 6 wherein the medium contains particles that are formed of abrasive materials or are provided with abrasive materials on outer surfaces thereof.

9. Method according to claim 6 wherein the size of the particles is uniform.

10. Method according to claim 6 wherein the size of the particles varies.

11. Method of claim 1 comprising the step of continuously feeding the medium.

12. Method of claim 1 comprising the step of alternatingly increasing and decreasing the pressure in the medium.

13. Method for removing caries in a cavity, comprising the steps of:
    (a) providing a flowable medium which contains at least one of a carries-dissolving substance and solid particles;
    (b) filling said cavity with said solid medium through a feed device having a supply line and a discharge line communicating with said flowable medium and said cavity, respectively;
    (c) feeding said medium into said filled cavity by said feed device; and,
    (d) initiating oscillation of the medium located in the cavity by means of an oscillation element of the feed device.

14. Method of claim 13 comprising the step of continuously feeding the medium.

15. Method of claim 13 comprising the step of alternatingly increasing and decreasing the pressure in the medium.

16. Method of claim 13 wherein the medium contains abrasive solid particles.

17. Method of claim 13 wherein the medium contains solid particles in sufficient quantity that the particles mutually contact one another in the cavity.

18. Method of claim 13 wherein when the cavity is initially of insufficient size to carry out said method, and the method comprises the further step of pre-preparing the cavity.

19. The method of claim 18 wherein said pre-preparing step is carried out with a rotating or oscillating tool.

20. Method according to claim 13, wherein the medium contains a caries-dissolving substance and/or particles.

21. Method according to claim 20 wherein the particles are abrasive.

22. Method according to claim 20 wherein the medium contains particles that are formed of abrasive materials or are provided with abrasive materials on outer surfaces thereof.

23. Method according to claim 20 wherein the size of the particles is uniform.

24. Method according to claim 20 wherein the size of the particles varies.

* * * * *